(12) United States Patent
Arai et al.

(10) Patent No.: US 12,721,655 B2
(45) Date of Patent: Sep. 1, 2026

(54) IMPLANT FOR BONE FRACTURE TREATMENT AND METHOD FOR MANUFACTURING IMPLANT FOR BONE FRACTURE TREATMENT

(71) Applicant: FUJI FILTER MANUFACTURING CO., LTD., Tokyo (JP)

(72) Inventors: Satoshi Arai, Tokyo (JP); Takashi Matsumoto, Tokyo (JP)

(73) Assignee: FUJI FILTER MANUFACTURING CO., LTD., Tokyo (JP)

( * ) Notice: Subject to any disclaimer, the term of this patent is extended or adjusted under 35 U.S.C. 154(b) by 1003 days.

(21) Appl. No.: 17/760,037

(22) PCT Filed: Oct. 30, 2020

(86) PCT No.: PCT/JP2020/040851
§ 371 (c)(1),
(2) Date: Aug. 3, 2022

(87) PCT Pub. No.: WO2021/157145
PCT Pub. Date: Aug. 12, 2021

(65) Prior Publication Data

US 2023/0041443 A1 Feb. 9, 2023

(30) Foreign Application Priority Data

Feb. 5, 2020 (JP) ................................ 2020-018187
Jul. 16, 2020 (JP) ................................ 2020-122099

(51) Int. Cl.
*A61B 17/68* (2006.01)
*A61B 17/00* (2006.01)

(52) U.S. Cl.
CPC .... *A61B 17/68* (2013.01); *A61B 2017/00004* (2013.01)

(58) Field of Classification Search
CPC ..................................................... A61B 17/68
See application file for complete search history.

(56) References Cited

U.S. PATENT DOCUMENTS 8,734,526 B2 * 5/2014 Adzich ................. A61F 2/0063 623/23.72
8,956,394 B1 * 2/2015 McDonnell ............. D04C 1/06 606/86 R (Continued)

FOREIGN PATENT DOCUMENTS

JP S53-41093 A 4/1978
JP 2004-305734 A 11/2004

(Continued)

OTHER PUBLICATIONS

WIPO, Japanese International Search Authority, International Search Report with English Translation and International Written Opinion mailed on Jan. 12, 2021 in International Patent Application No. PCT/JP2020/040851, 11 pages.

*Primary Examiner* — Christian A Sevilla
(74) *Attorney, Agent, or Firm* — MASUVALLEY & PARTNERS; Peter Martinez

(57) ABSTRACT

A new implant for bone fracture treatment that can easily and securely fix bone fragments is provided. An implant for bone fracture treatment that covers bone fragments gathered at a site to be treated for a bone fracture in a living body and reduces and fixes the site invasively includes a metal knit portion formed by knitting a metal string constituted by one or a plurality of biocompatible metal string elements into a cylindrical shape by circular knitting. The implant further includes a resin knit portion formed by knitting a resin string constituted by one or a plurality of biocompatible resin string elements into a cylindrical shape by circular knitting.

(Continued)

The metal knit portion and the resin knit portion are knitted to be continuous in an axial direction.

13 Claims, 13 Drawing Sheets

(56) References Cited

U.S. PATENT DOCUMENTS

| | | | | |
|---|---|---|---|---|
| 2004/0225291 | A1 | 11/2004 | Schwammberger et al. | |
| 2008/0255560 | A1 | 10/2008 | Myers et al. | |
| 2009/0024147 | A1 * | 1/2009 | Ralph | A61F 2/36 606/151 |

FOREIGN PATENT DOCUMENTS

| | | | |
|---|---|---|---|
| JP | 2008-500140 | A | 1/2008 |
| JP | 2010-524642 | A | 7/2010 |
| JP | 2010-533551 | A | 10/2010 |
| WO | 2008/134287 | A2 | 4/2008 |

* cited by examiner (a)

(b)

(c)

(a)

1(10)

11

CIRCUMFERENTIAL DIRECTION

ONE END PART

AXIAL DIRECTION

OTHER END PART (b)

(a)

1E
10b(1b)
20E
10
10c
11
WIDTH DIRECTION
AXIAL DIRECTION (b)

1F
10b(1b)
20F
10
10c
11
CIRCUMFERENTIAL DIRECTION
13
WIDTH DIRECTION
AXIAL DIRECTION (a)

(b)

(c)

(a)

(b)

( a )

( b )

( c )

IMPLANT FOR BONE FRACTURE TREATMENT AND METHOD FOR MANUFACTURING IMPLANT FOR BONE FRACTURE TREATMENT

RELATED APPLICATIONS

This application is the U.S. National Phase of and claims priority to International Patent Application No. PCT/JP2020/040851, International Filing Date Oct. 30, 2020; which claims benefit of Japanese Patent Application No. 2020-018187 filed Feb. 5, 2020; and of Japanese Patent Application No. 2020-122099 filed Jul. 16, 2020 all of which are incorporated herein by reference in their entireties.

FIELD

The present invention relates to an implant for bone fracture treatment that covers bone fragments (fractured bone fragments) gathered at a site to be treated for a bone fracture in a living body and reduces and fixes the site invasively, and particularly to an implant with a metal knit portion formed of a metal string.

BACKGROUND

The following methods are known as a method for reducing a fractured part invasively.

1. Pinning

Pinning is a surgery method in which a pin formed of a K-wire (Kirschner wire) or the like is inserted into a fractured part to fix bone fragments to each other at normal positions. The pinning is selected for a simple bone fracture such as when bone fragments are displaced from their normal positions due to the bone fracture.

2. Screw Fixation

Screw fixation is a surgery method in which bone fragments are fixed only with a screw. The screw fixation is selected for a simple bone fracture.

3. Plate Fixation

Plate fixation is a surgery method in which bone fragments are fixed with a plate and a screw. The plate fixation is selected in a case where a bone forming a joint and/or a bone near the joint is fractured.

4. External Fixation

External fixation is a method for fixing bone fragments from outside the body using a pin, a wire, and the like. The external fixation is selected for an open fracture, an intra-articular fracture, a crushed fracture of a bone that cannot be fixed with a plate and a screw, or the like.

5. Intramedullary Nail Fixation

Intramedullary nail fixation is a method in which an intramedullary nail (nail) is inserted into bone marrow to fix bone fragments. The intramedullary nail fixation is mainly selected when the diaphysis of a large bone such as a humerus, a femur, or a tibia is fractured.

Patent Literature 1 discloses an implant for bone fracture treatment that is used for a proximal humerus fracture. This implant is used for the plate fixation described in 3 and is made of, for example, titanium.

The implant described in Patent Literature 1 includes a strip-shaped main plate to be fixed to one surface of a fractured part, an outrigger plate that is to be fixed to the other surface (opposite surface) of the fractured part and sandwiches the fractured part together with the main plate, and two linear connecting elements that connect both of the plates to each other.

The two linear connecting elements extend in parallel from appropriate positions on a side edge of the outrigger plate along the plate surface. In the main plate, two holes through which the linear connecting elements described above are inserted are formed along the direction of the shorter side of the implant. Distal end parts of the two connecting elements are exposed to the outside from the holes of the main plate.

The main plate and the outrigger plate can be flexibly deformed to shapes in which the plates can be placed at a fractured part. The main plate is placed on one surface of a fractured part and fixed to the one surface by a screw, the outrigger plate is placed on the other surface of the fractured part and fixed to the other surface by a screw, and the distal end parts of the two connecting elements exposed from the main plate are twisted to prevent the connecting elements from being pulled out of the main plate and fix the distance between the main plate and the outrigger plate.

CITATION LIST

Patent Literature

Patent Literature 1: Japanese Patent Application Laid-open No. 2004-305734

SUMMARY

Technical Problem

In a case where a patella, an olecranon, a calcaneus, or a greater trochanter of femur is crushed and fractured, any of the above methods described in 3 to 5 is selected. However, bone fracture treatment using only the methods described in 3 to 5 is very difficult. That is, when a bone is crushed and fractured, bone fragments are about several millimeters in size. Since the way in which a fracture line enters and the shapes of the bone fragments differ from patient to patient, it is necessary to determine a method for fixing the bone fragments, a position where a screw is inserted, and the like for each patient.

For such reasons, surgery time required to treat crushed and fractured parts tends to be long. Meanwhile, there is a demand to shorten the surgery time and reduce surgery costs. That is, a new implant for bone fracture treatment that can easily and securely fix bone fragments has been demanded.

The present invention has been achieved in view of the above problems and an object of the present invention is to provide a new implant for bone fracture treatment that can easily and securely fix bone fragments.

Solution to Problem

In order to solve the above problems, the present invention provides an implant for bone fracture treatment that covers bone fragments gathered at a site to be treated for a bone fracture in a living body and reduces and fixes the site invasively, comprising a metal knit portion formed by knitting a metal string constituted by one or a plurality of biocompatible metal string elements into a cylindrical shape by circular knitting.

Advantageous Effects of Invention

According to the present invention, a new implant for bone fracture treatment that can easily and securely fix bone fragments can be provided.

DESCRIPTION OF EMBODIMENTS

Figure 1:
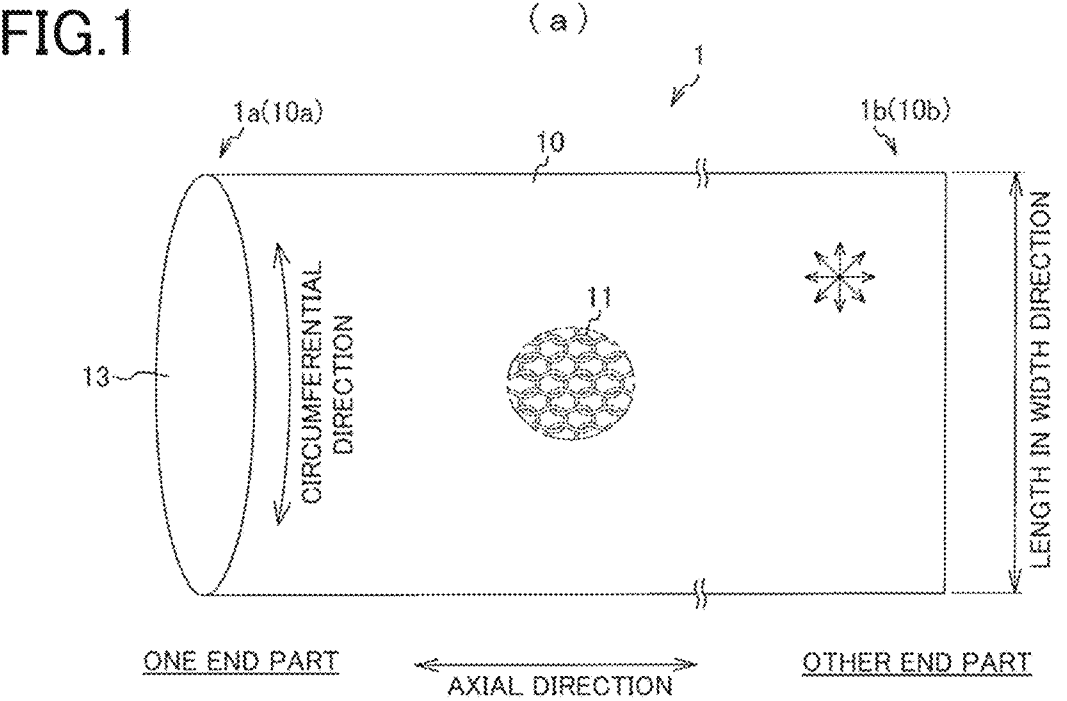
FIG. 1 are diagrams illustrating an implant according to a first embodiment of the present invention, where FIG. 1(*a*) is a perspective view illustrating a schematic configuration of the implant, and FIGS. 1(*b*) and 1(*c*) are diagrams illustrating shape examples after deformation.
Figure 1:
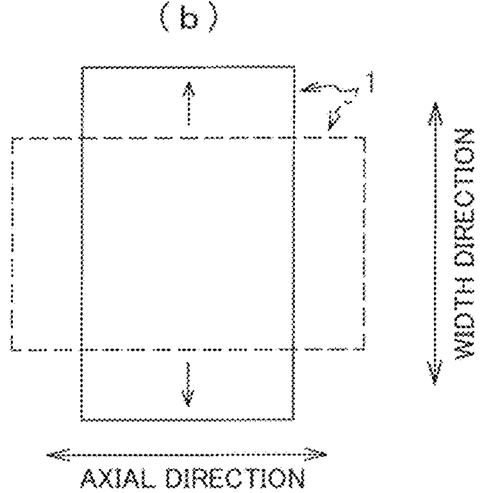
Figure 1:
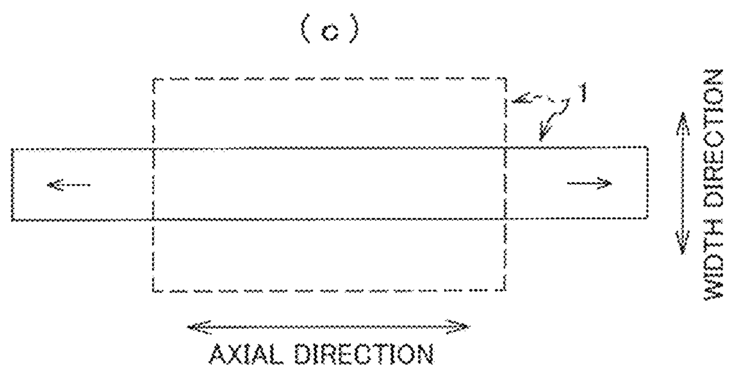

The present invention will be explained in detail below using embodiments illustrated in the drawings. Constituent elements, types, combinations, shapes, and relative arrangements in the embodiments are, unless otherwise specified, not intended to limit the scope of the present invention solely thereto but are merely explanatory examples.

First Embodiment

FIG. 1 are diagrams illustrating an implant according to a first embodiment of the present invention. FIG. 1(*a*) is a perspective view illustrating a schematic configuration of the implant, and FIGS. 1(*b*) and 1(*c*) are diagrams illustrating shape examples after deformation.

An implant 1 according to the present embodiment is used for bone fracture treatment. The implant 1 is used to cover bone fragments (or fractured bone fragments) gathered at a fractured part in a living body, for example. The fractured part is a site to be treated for the bone fracture. The implant 1 reduces and fixes the fractured part invasively.

The implant 1 includes a metal knit portion 10 (a wire knit mesh portion) formed by knitting a metal string 11 constituted by one or a plurality of biocompatible metal string elements. The entirety of the implant 1 according to the present embodiment is constituted by the metal knit portion 10.

<Metal Knit Portion>

«Exterior Configuration»

The implant 1 is formed by knitting the fibrous metal string 11 into a cylindrical shape using a circular knitting machine. The implant 1 is knitted into a cylindrical shape with a series of spirally formed loops (needle loops and sinker loops). The implant 1 illustrated in FIG. 1(*a*) is knitted from one end side to the other end side in its axial direction.

The implant 1 is made of a weft knitted fabric. That is, the circumferential direction of the implant 1 is the same as the course direction of the knitted fabric and the axial direction of the implant 1 is the same as the wale direction of the knitted fabric.

The implant 1 is used in a shape in which the knitted fabric are doble-layered by overlapping (placing in close contact) parts of an inner circumferential faces 13 facing each other. It is assumed that the initial shape of the implant 1 is a rectangular cloth-like shape. Hereinafter, the initial shape of the implant 1 will be described as a rectangular shape. The length (the length in a direction orthogonal to the axial direction) of the implant 1 in the initial shape in its width direction is, for example, half the length of the implant 1 in its circumferential direction at the time of completion of knitting.

Since the implant 1 is constituted by the Knitted fabrics, the implant 1 can be expanded and contracted in its axial direction, its width direction, and a direction intersecting the axial direction and the width direction. The implant 1 is used in the initial shape or in a shape appropriately deformed from the initial shape.

In each of FIGS. 1(*b*) and 1(*c*), a broken line represents the initial shape of the implant 1 and a solid line represents a deformed shape of the implant 1.

As illustrated in FIG. 1(*b*), the implant 1 can be used for bone fracture treatment in a shape deformed from the initial shape and expanding in the width direction. In this deformed shape, the implant 1 is contracted in the axial direction.

As illustrated in FIG. 1(*c*), the implant 1 can be used for bone fracture treatment in a shape deformed from the initial shape and expanding in the axial direction. In this deformed shape, the implant 1 is contracted in the width direction. When the implant 1 is expanded in the axial direction, the implant 1 can be used also as a string.

Alternatively, the implant 1 can be used for bone fracture treatment in a shape deformed from the rectangular initial shape and further folded in two, folded in three, or the like.

Since the implant 1 is constituted by the Knitted fabrics, the implant 1 is a three-dimensional structure with a predetermined thickness. In addition, the implant 1 has many holes due to many loops formed by the metal string and thus is a porous structure.

«Metal String»

As the metal constituting the implant 1, biocompatible metal that can be left in a human body is used. For example, as the metal constituting the implant 1, pure titanium, titanium alloy, titanium-nickel alloy, stainless steel, cobalt-chromium alloy, tantalum, precious metal alloy, or the like can be used. As the metal constituting the implant 1, pure titanium or titanium alloy is particularly preferable.

Figure 2:
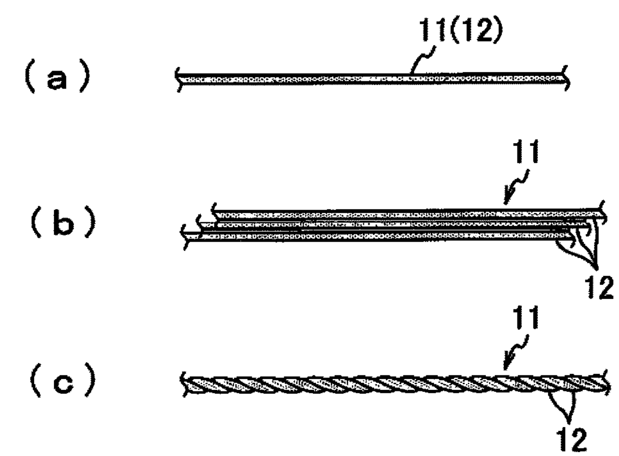
FIGS. 2(*a*) to 2(*c*) are schematic diagrams illustrating configuration examples of metal strings.

FIGS. 2(*a*) to 2(*c*) are schematic diagrams illustrating configuration examples of the metal string.

As illustrated in FIG. 2(*a*), the metal string 11 may be constituted by a single metal string element 12. That is, the metal knit portion 10 may be knitted from a single metal string element 12 as a monofilament.

As illustrated in FIG. 2(*b*), the metal string 11 may be constituted by a plurality of gathered metal string elements 12, 12, . . . . The plurality of gathered metal string elements 12, 12, . . . may not be twisted together. That is, the metal knit portion 10 may be knitted from the plurality of multi-strand metal string elements 12, 12, . . . . The multi-strand metal string elements 12, 12, are bundled metal string elements or untwisted metal string elements.

As illustrated in FIG. 2(*c*), the metal string 11 may be constituted by the plurality of gathered metal string elements 12, 12, . . . . The plurality of gathered metal string elements 12, 12, . . . may be twisted together. That is, the metal knit portion 10 may be knitted from the metal string 11 as a stranded wire string.

From the viewpoint of ensuring the flexibility of the implant 1 and/or from the viewpoint of preventing stress shielding, it is preferable that the metal knit portion 10 be formed of a single metal string element 12 or a plurality of multi-strand metal string elements 12, 12, . . . .

As the metal string element 12, a round wire string with a circular sectional shape is used. When the metal string element 12 is a round wire string, it is preferable that the wire diameter (diameter) of the metal string element 12 be in a range from Ø0.06 mm to Ø0.70 mm, for example. When the metal string 11 is constituted by a plurality of metal string elements 12, 12, . . . , it is preferable that the outer diameter (diameter) of the metal string 11 be equal to or smaller than Ø0.70 mm.

When the metal string elements 12 with such wire diameter are used, the implant 1 is flexibly curved and deformed (or bent and deformed) according to the shape of a reduced fractured part. Using the metal string elements 12 with such wire diameter prevents occurrence of stress shielding.

As the implant 1, a metal string element 12 having a sectional shape other than a circular sectional shape may be used.

«Knitted Fabrics»

As the implant 1, it is possible to use knitted fabrics formed according to the three basic types of knitting, plain stitch knitting, rib stitch knitting, and purl stitch knitting, or a combination of these types of knitting as needed.

The wire diameter and the sectional shape of the metal string 11 (or the metal string elements 12), the length of the implant 1 in the initial shape in the width direction, the stitch density of the implant 1, the type of the knitted fabric, and the like are set according to an in-vivo site where the implant 1 is used, required amounts of expansion and contraction of the implant 1, and the like as appropriate.

The length of the implant 1 in the initial shape in the width direction and the length of the implant 1 in the initial shape in the axial direction are determined based on the size that can cover a site to be treated.

When the implant 1 is used for treatment of a patella fracture, an olecranon fracture, a calcaneal fracture, a greater trochanteric femoral fracture, or the like, it is preferable that the length of the implant 1 in the initial shape in the width direction be in a range from 10 mm to 60 mm, for example.

The length of the implant 1 in the initial shape in the axial direction can be adjusted to any length according to the number (the number of steps) of stitches formed in the axial direction. In addition, it is desirable that the length of the implant 1 in the initial shape in the axial direction be arbitrarily determined according to its usage, such as according to whether the implant 1 covers only the surface of a fractured part or is wrapped around an entire bone including the fractured part and surroundings of the fractured part and surrounds the bone, or the like.

EXAMPLE OF REAL IMAGES

Figure 3:
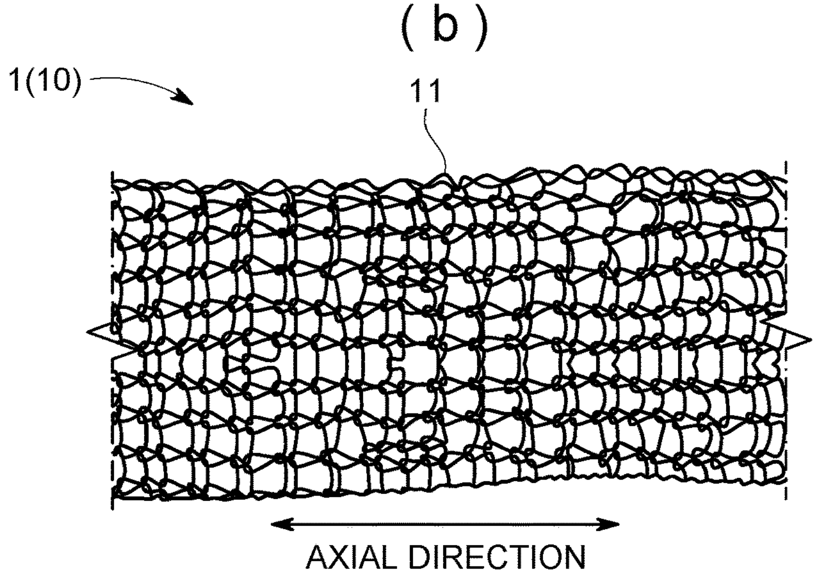
FIG. 3 are diagrams illustrating real images of the implant according to the first embodiment of the present invention, where FIG. 3(*a*) is a diagram illustrating an image of the entire implant, and FIG. 3(*b*) is a diagram illustrating an enlarged image of an end part in the width direction.

FIG. 3 are diagrams illustrating real images of the implant according to the first embodiment of the present invention. FIG. 3(*a*) is a diagram illustrating an image of the entire implant, and FIG. 3(*b*) is a diagram illustrating an enlarged image of an end part in the width direction.

The implant 1 illustrated in FIG. 3 is formed by knitting the metal string 11 as a monofilament made of pure titanium with a wire diameter of Ø0.5 mm according to plain stitch knitting. The implant 1 illustrated in FIG. 3 is neither expanded nor contracted in the axial direction and the width direction and is in a state after an axial end of the metal string is cut and the implant 1 is taken out from a circular knitting machine. The length of the implant 1 illustrated in FIG. 3 in the circumferential direction is 64 mm, while the length thereof in the axial direction is 130 mm.

«End-Part Treatment»

End-part treatment is performed on an end part of the metal knit portion 10 constituting the implant 1 in the axial direction as needed. An example of the end-part treatment is described later.

<Manufacturing of Implant>

Figure 4:
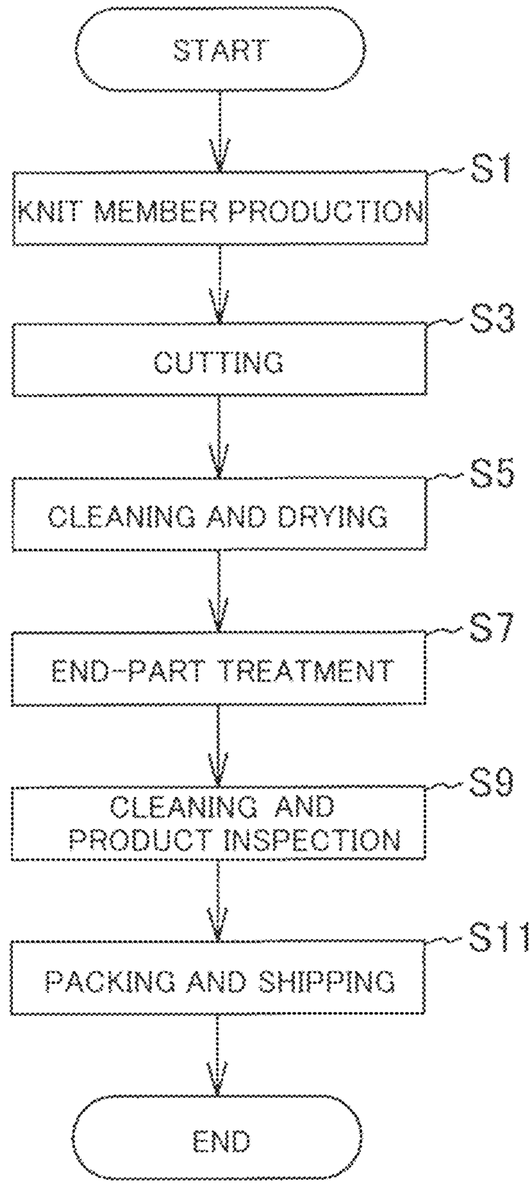
FIG. 4 is a flowchart illustrating an example of a manufacturing process of the implant.

FIG. 4 is a flowchart illustrating an example of a manufacturing process of the implant.

<S1: Knit Member Producing Process>

In a knit member producing process, a circular knitting machine that supports metal strings is used to circularly knit the metal string to knit a cylindrical metal knit fabrics that is the precursor of the implant.

As the circular knitting machine for circularly knitting metal strings, a "wire mesh knitting machine" described in JP 3178575 U can be used.

The operating principle of the wire mesh knitting machine that circularly knits metal strings is the same as that of a circular knitting machine that circularly knits fiber strings. The circular knitting machine is a known machine and descriptions thereof will be omitted.

<S3: Cutting Process>

In a cutting process, the produced cylindrical metal knit portion is taken out from the circular knitting machine. That is, the metal string 11 forming the metal knit portion is cut to obtain a metal knit member with a predetermined length in the axial direction.

<S5: Cleaning and Drying Process>

After an acid cleaning solution adhering to the surface of the metal knit member is removed by cleaning, the metal knit member is dried.

The metal knit member subjected to this process may be completed as the implant, but processes of Step S9 and the subsequent step are performed as needed.

<S7: End-Part Treatment Process>

Predetermined end-part processing is performed on at least an end part of the metal knit member in the axial direction on the knitting end side.

End-part treatment is performed to prevent the metal string 11 from fraying (unraveling). The end-part treatment is performed to add a predetermined function to the implant 1, depending on its mode.

<S9: Cleaning and Product Inspecting Process>

In a cleaning and product inspecting process, the implant 1 is cleaned as needed. In addition, whether the implant 1 satisfies a predetermined product condition is inspected.

<S11: Packing and Shipping Process>

Lastly, the implant is packed and shipped. In this process, sterilization treatment is performed on the implant 1 after the packing as needed.

EXAMPLE OF END-PART PROCESSING

Predetermined end-part processing is performed on an end part of the metal knit portion 10 (the metal knit member at Steps S7 and 9) in the axial direction as needed.

The primary purpose of the end-part processing is to certainly prevent the metal knit portion 10 from fraying. However, since the metal string 11 can keep its curved or bent and deformed shape, the shape of the loop at the final stage is kept to some extent without the end-part processing. Therefore, the end-part processing is arbitrarily performed for the purpose of preventing fraying. For the purpose of preventing fraying, the end-part processing is performed on at least an end part 10*b* on the knitting end side, but may be performed on both end parts in the axial direction.

The secondary purpose of the end-part processing is to add, to the implant 1, a function that cannot be obtained only by the metal knit portion 10 according to the treatment mode of the end-part processing. For the purpose of adding the function, the end-part processing is performed on any or both of the end parts 10*a* and 10*b* (see FIG. 1) of the metal knit portion 10 in the axial direction according to a part to which the function is to be added.

The following end-part processing examples can be used in combination as appropriate. In addition, end-part processing to be performed on one of the end parts of the metal knit portion 10 in the axial direction may be different from end-part processing to be performed on the other end part of the metal knit portion 10 in the axial direction.

FIRST EXAMPLE OF END-PART PROCESSING

Figure 5:
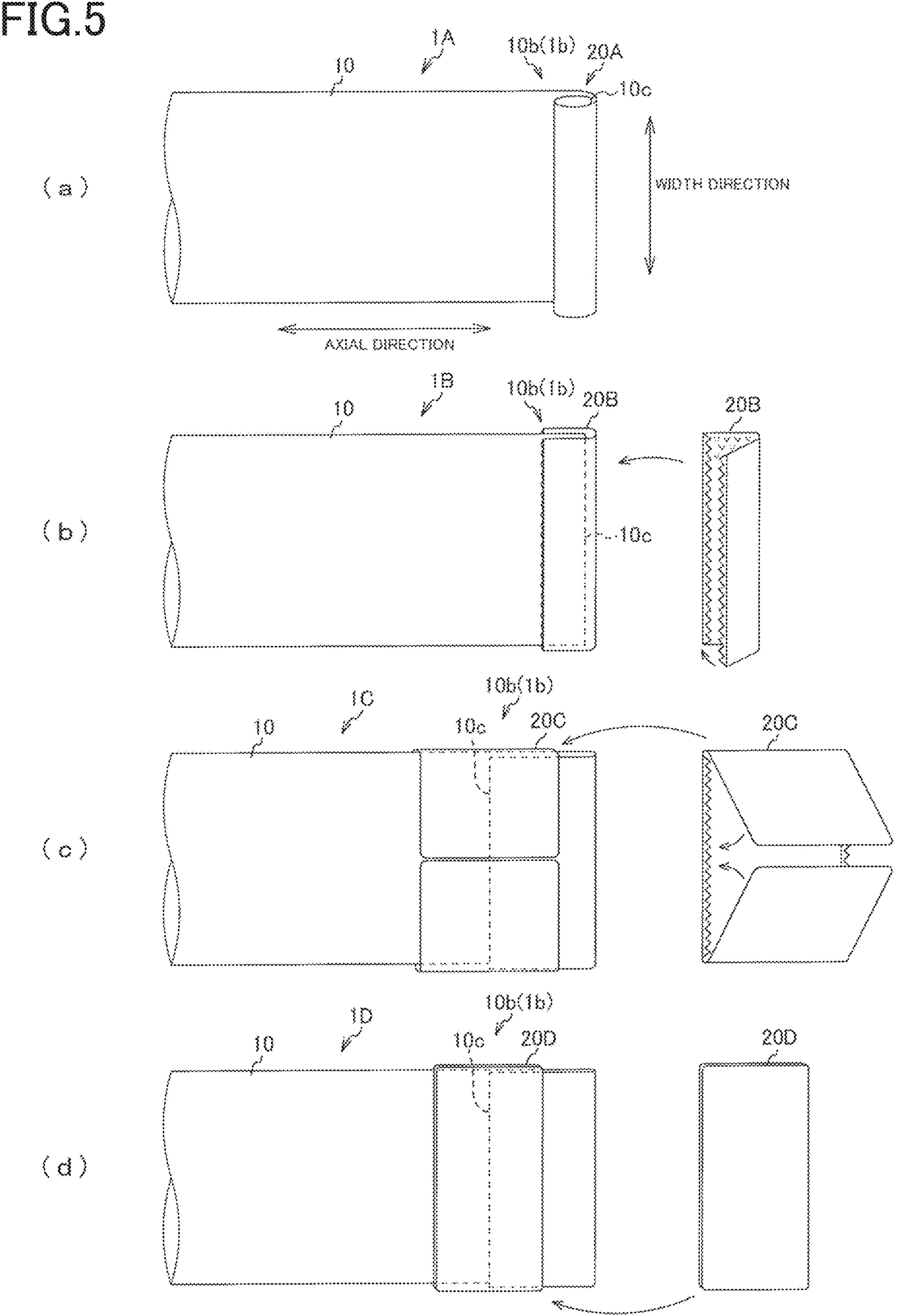
FIGS. 5(*a*) to 5(*d*) are schematic diagrams illustrating examples of end-part processing of a metal knit portion.

FIGS. 5(*a*) to 5(*d*) are schematic diagrams illustrating examples of the end-part processing of the metal knit portion. End-part processing illustrated in the drawings prevents an edge 10*c* of the metal knit portion 10 from being exposed to the outside and thus can prevent the metal knit portion 10 from fraying.

An implant 1A illustrated in FIG. 5(*a*) includes an end-part processing portion 20A formed by folding the end part 10*b* of the metal knit portion 10 in three. That is, the end-part processing portion 20A extends in the width direction of the metal knit portion 10 and is formed by folding the end part of the metal knit portion 10 along two fold lines separated from each other in the axial direction of the metal knit portion 10 such that the end part of the metal knit portion 10 is wrapped. After the end part 10*b* of the metal knit portion 10 is folded in three, the end part 10*b* may be fixed by brazing, resistance welding, an adhesive, or the like such that the end part 10*b* does not turn over.

An implant 1B illustrated in FIG. 5(*b*) has a fastening tool 20B attached to the end part 10*b* of the metal knit portion 10. For example, the fastening tool 20B sandwiches the end part 10*b* of the metal knit portion 10 and is tightened to cover a part of the metal knit portion 10 that has a predetermined length from an axial edge 10*c* of the metal knit portion 10. When the fastening tool 20B has biocompatibility, the fastening tool 20B may be made of metal or synthetic resin. The fastening tool 20B may be fixed to the metal knit portion 10 by brazing, resistance welding, an adhesive, or the like.

An implant 10 illustrated in FIG. 5(*c*) has a fastening tool 20C attached to the end part 10*b* of the metal knit portion 10. For example, the fastening tool 20C sandwiches an appropriate portion of the end part 10*b* of the metal knit portion 10 folded back in the axial direction and is tightened to cover a part of the metal knit portion 10 that includes the edge 10*c* of the metal knit portion 10 and has a predetermined length in the axial direction such that the part is not exposed to the outside. When the fastening tool 20C has biocompatibility, the fastening tool 20C may be made of metal or synthetic resin. The fastening tool 20C may be fixed to the metal knit portion 10 by brazing, resistance welding, an adhesive, or the like.

An implant 1D illustrated in FIG. 5(*d*) has a fastening tool 20D attached to one surface of the end part 10*b* of the metal knit portion 10. The fastening tool 20D has a plate shape and is placed at and fixed to an appropriate portion of the end part 10*b* to cover the edge 10*c* of the metal knit portion 10 folded back in the axial direction. When the fastening tool 20D has biocompatibility, the fastening tool 20D may be made of metal or synthetic resin.

The fastening tool 20D is fixed to the end part 10*b* of the metal knit portion 10 by brazing, resistance welding, an adhesive, or the like according to the constituent material of the fastening tool 20D. The fastening tool 20D covers the edge 10*c* of the metal knit portion 10 such that the edge 10*c* is not exposed to the outside.

In this manner, the implant 1 is processed such that the edge 10*c* of the metal knit portion 10 is not exposed to the outside. The end-part processing examples described above are examples in which the end-part processing is performed without changing the length of the implant 1 (the metal knit portion 10) in the initial shape in the width direction.

SECOND EXAMPLE OF END-PART PROCESSING

Figures 6, 7:
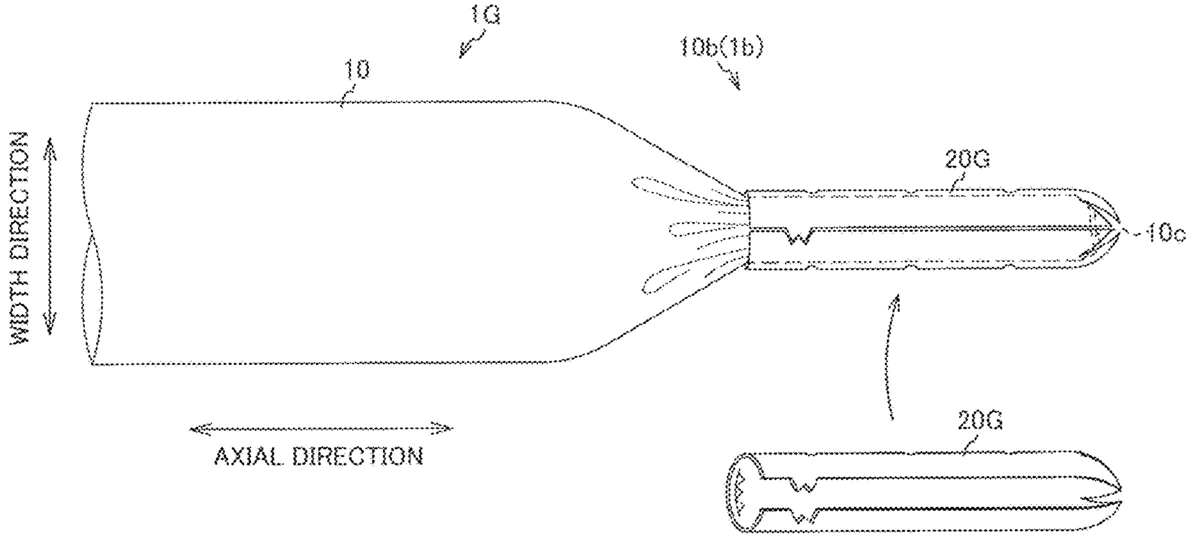
FIGS. 6(*a*) and 6(*b*) are schematic diagrams illustrating examples of the end-part processing of the metal knit portion.
FIG. 7 is a schematic diagram illustrating an example of the end-part processing of the metal knit portion.

FIGS. 6(*a*) and 6(*b*) are schematic diagrams illustrating examples of the end-part processing of the metal knit portion.

Implants 1E and 1F illustrated in FIGS. 6(*a*) and 6(*b*) have end-part processing portions 20E and 20F formed by causing synthetic resin to adhere to end parts of the implants 1. Each of the end-part processing portions 20E and 20F is formed by dipping the end part 10*b* of the metal knit portion 10 into melted synthetic resin and solidifying the synthetic resin. This processing example is an example in which the end-part processing is performed without changing the length of the implant 1 (the metal knit portion 10 in this case) in the initial shape in the width direction.

As illustrated in FIG. 6(*a*), the end-part processing portion 20E may be formed in a state in which parts forming an inner circumferential face 13 of the metal knit portion 10 are in close contact with each other. As illustrated in FIG. 6(*b*), the end-part processing portion 20F may be formed in a state in which parts forming the inner circumferential face 13 of the metal knit portion 10 are not in close contact with each other, that is, the end part 10*b* of the metal knit portion 10 is kept in a cylindrical shape.

The end-part processing portions 20E and 20F illustrated in FIGS. 6(*a*) and 6(*b*) keep parts of the metal string 11 in close contact with each other or keep the parts of the metal string 11, which are not in close contact with each other, close to each other. By forming the end-part processing portions 20E and 20F in this manner, flexible movement of the metal string 11 is limited. By appropriately adjusting any or all of the viscosity of the synthetic resin at the time of dipping, the thickness of the synthetic resin covering the metal string 11, the elasticity of the synthetic resin after hardening, and the like, predetermined deformability may be given to the end-part processing portions 20E and 20F.

THIRD EXAMPLE OF END-PART PROCESSING

FIG. 7 is a schematic diagram illustrating an example of the end-part processing of the metal knit portion.

An implant 1G illustrated in FIG. 7 has a fastening tool 20G attached to the end part 10*b* of the metal knit portion 10. The fastening tool 20G covers the end part 10*b* of the metal knit portion 10 to prevent the edge 10*c* of the metal knit portion 10 from being exposed to the outside. The fastening tool 20G prevents the implant from fraying. The fastening tool 20G makes an axial end part of the implant 1 tapered.

When the fastening tool 20G has biocompatibility, the fastening tool 20G may be made of metal or synthetic resin.

The fastening tool 20G is fixed to the metal knit portion 10 by tightening, brazing, resistance welding, an adhesive, or the like.

In this example, since the axial end part of the implant 1G has a tapered shape, it is possible to insert the fastening tool 20G into an appropriate part of the metal knit portion 10, a hole formed in another plate for bone fracture treatment, another hole, and a gap. In addition, it is possible to use the fastening tool 20G to fasten the implant 1G placed at a fractured part such that the implant 1G does not loosen.

FOURTH EXAMPLE OF END-PART PROCESSING

Figure 8:
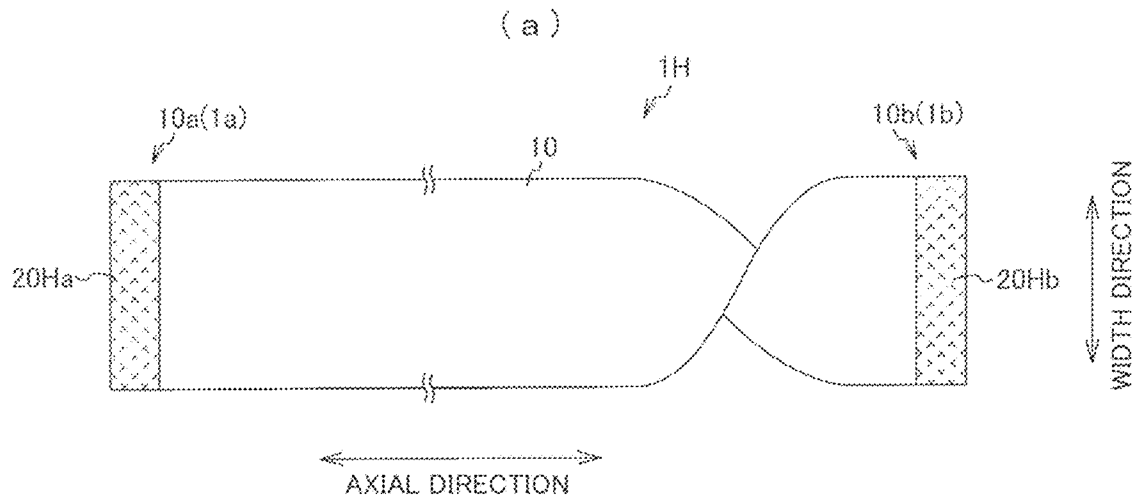
FIGS. 8(*a*) and 8(*b*) are schematic diagrams illustrating examples of the end-part processing of the metal knit portion, and FIG. 8(*c*) is a schematic sectional view illustrating a coupled state of snap coupling members illustrated in FIG. 8(*b*).
Figure 8:
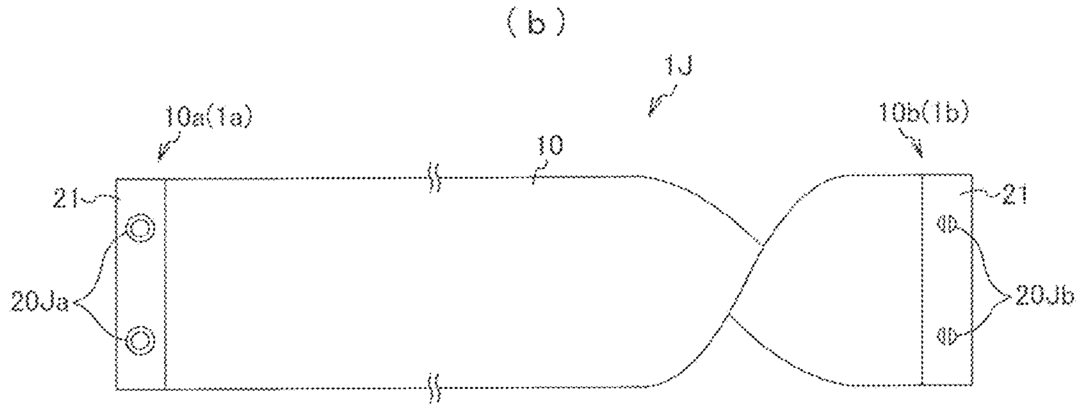
Figure 8:
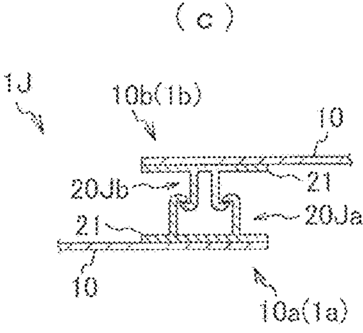

FIGS. 8(*a*) and 8(*b*) are schematic diagrams illustrating examples of the end-part processing of the metal knit portion. FIG. 8(*c*) is a schematic sectional view illustrating a coupled state of snap coupling members illustrated in FIG. 8(*b*). Each of implants described in this example has a pair of fastening tools at both end parts in the axial direction and has a configuration in which one of the fastening tools is detachably attachable to the other fastening tool. The pair of fastening tools is made of a biocompatible material. This processing example is an example in which the end-part processing is performed without changing the lengths of the implants 1H and 1J (metal knit portions 10 in this case) in their initial shapes in the width direction.

The implant 1H illustrated in FIG. 8(*a*) has a pair of hook-and-loop fasteners 20H (20Ha, 20Hb) attached to the end parts 10*a* and 10*b* of the metal knit portion 10. The one hook-and-loop fastener 20Ha is freely bonded to the other hook-and-loop fastener 20Hb and is freely separated from the other hook-and-loop fastener 20Hb. The hook-and-loop fasteners 20H are attached to the metal knit portion 10 by, for example, an adhesive.

The implant 1J illustrated in FIG. 8(*b*) has a pair of snap coupling members 20J (20Ja, 20Jb) attached to the end parts 10*a* and 10*b* of the metal knit portion 10. Each of the snap coupling members 20J projects from one surface of a plate-shaped base 21 in a direction (a direction orthogonal to the one surface in FIG. 8(*b*)) intersecting the one surface of the base 21. As illustrated in FIG. 8(*c*), the one snap coupling member 20Ja is coupled to the other snap coupling member 20Jb by being fitted to the other snap coupling member 20Jb. Furthermore, the one snap coupling member 20Ja can be freely separated from the other snap coupling member 20Jb. The snap coupling members 20J are attached to the metal knit portion 10 by bonding the base 21 to the metal knit portion 10 using, for example, an adhesive.

FIFTH EXAMPLE OF END-PART PROCESSING

Figure 13:
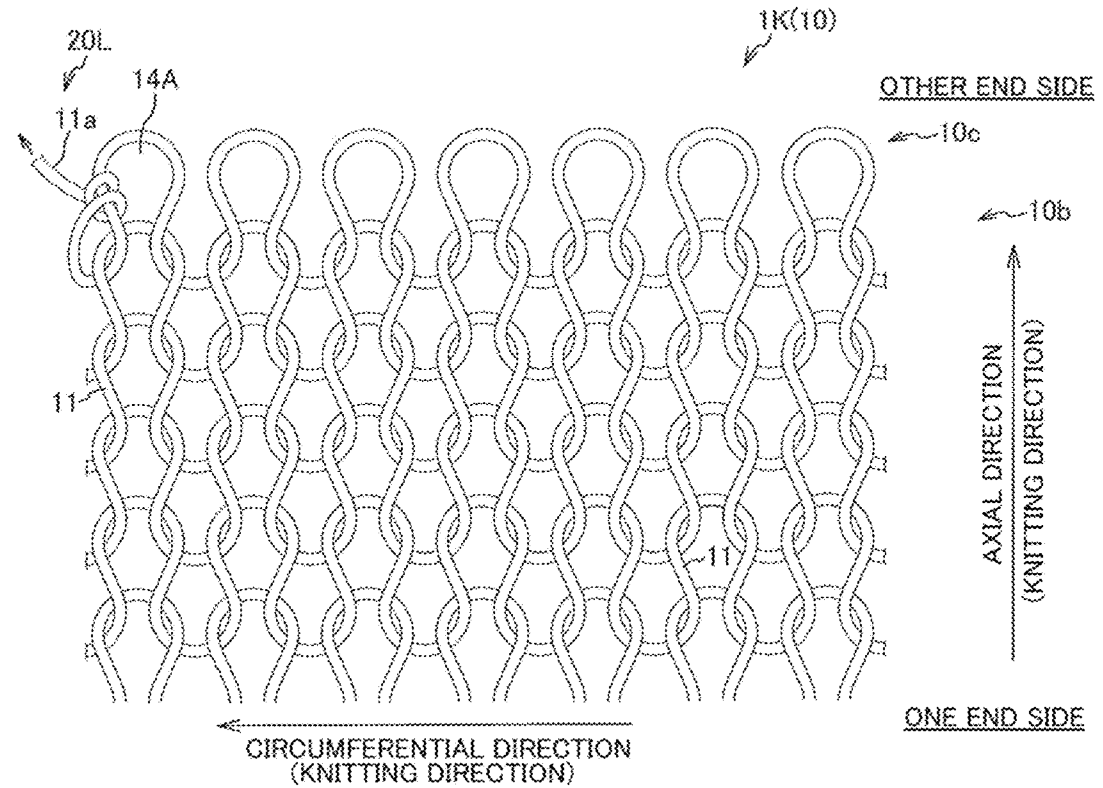
FIGS. 13(*a*) and 13(*b*) are schematic diagrams illustrating examples of the end-part processing of the metal knit portion.
Figure 13:
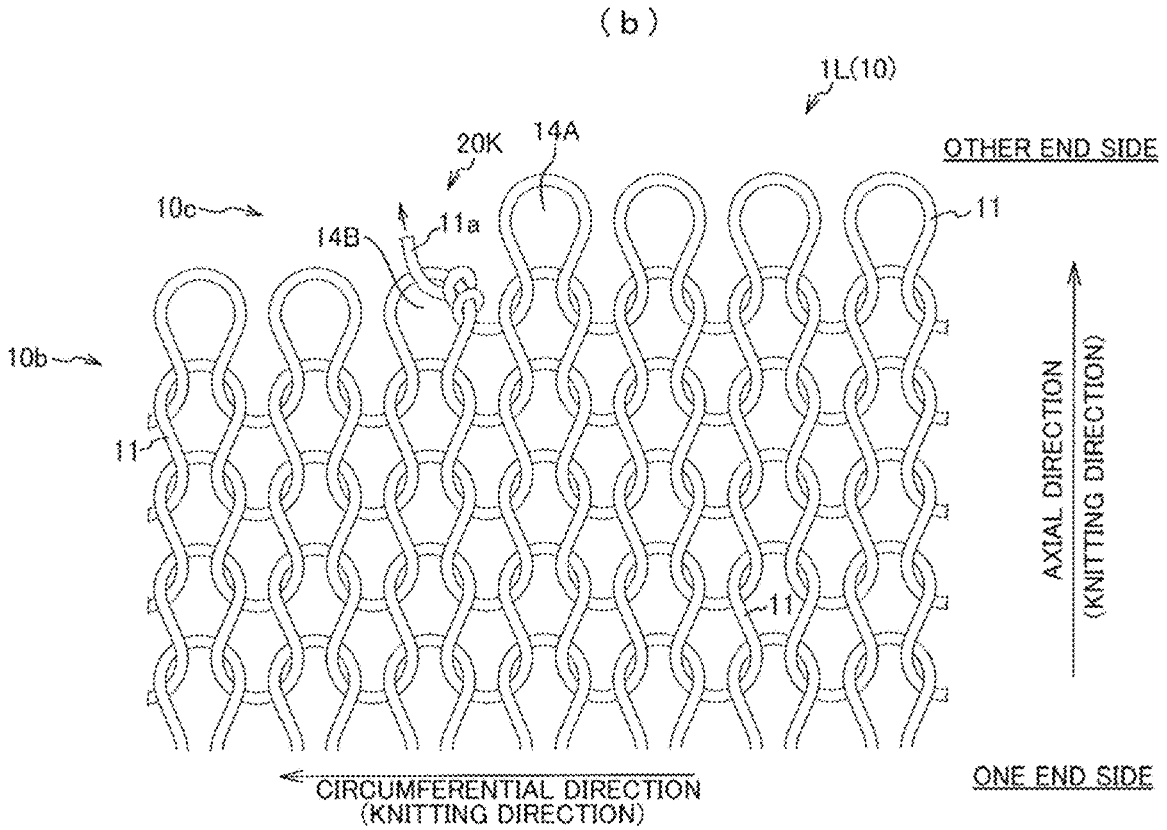

FIGS. 13(*a*) and 13(*b*) are schematic diagrams illustrating examples of the end-part processing of the metal knit portion.

Each of implants 1 (1K, 1L) illustrated in the examples is processed as end-part processing 20 (20K, 20L) to wind an end part 11*a* of the metal string 11 around at least one appropriate loop (a needle loop 14 (14A, 14B) or a sinker loop) positioned at an axial end part of the metal knit portion 10 and pull and tighten the end part 11*a* of the metal string 11. In each of FIGS. 13(*a*) and 13(*b*), the end part 10*b* of the metal knit portion on the knitting end side is illustrated as an example.

The implant 1K illustrated in FIG. 13(*a*) represents an example in which the end part 11*a* of the metal string 11 positioned on the distal end side with respect to the last needle loop 14A is wound around a part of the metal string 11 that forms the last needle loop 14A.

The implant 1L illustrated in FIG. 13(*b*) represents an example in which the end part 11*a* of the metal string 11 is wound around a part of the metal string 11 that forms a single needle loop 14B forming the axial edge 10*c*. In this example, the end part 11*a* is wound around the needle loop 14B at the previous stage adjacent to the last needle loop 14A.

To effectively prevent the metal string 11 from fraying, it is desirable that the end part 11*a* be wound around the loop 14 a plurality of times. In this example, the end part 11*a* is wound around the loop 14 twice. In addition, in a case where the end part 11*a* is wound around the loop 14, it is desirable that every time the end part 11*a* is wound around the loop 14, the end part 11*a* be strongly pulled and tightened in a direction (a direction indicated by an arrow in each of FIGS. 13(*a*) and 13(*b*)) toward a distal end of the metal string 11 such that each "ring" of the end part 11*a* formed around the loop 14 is sufficiently small. When each "ring" formed by the end part 11*a* is sufficiently small, the plastic deformation of the metal string 11 can more effectively prevent the metal knit portion 10 from fraying.

Figure 16:
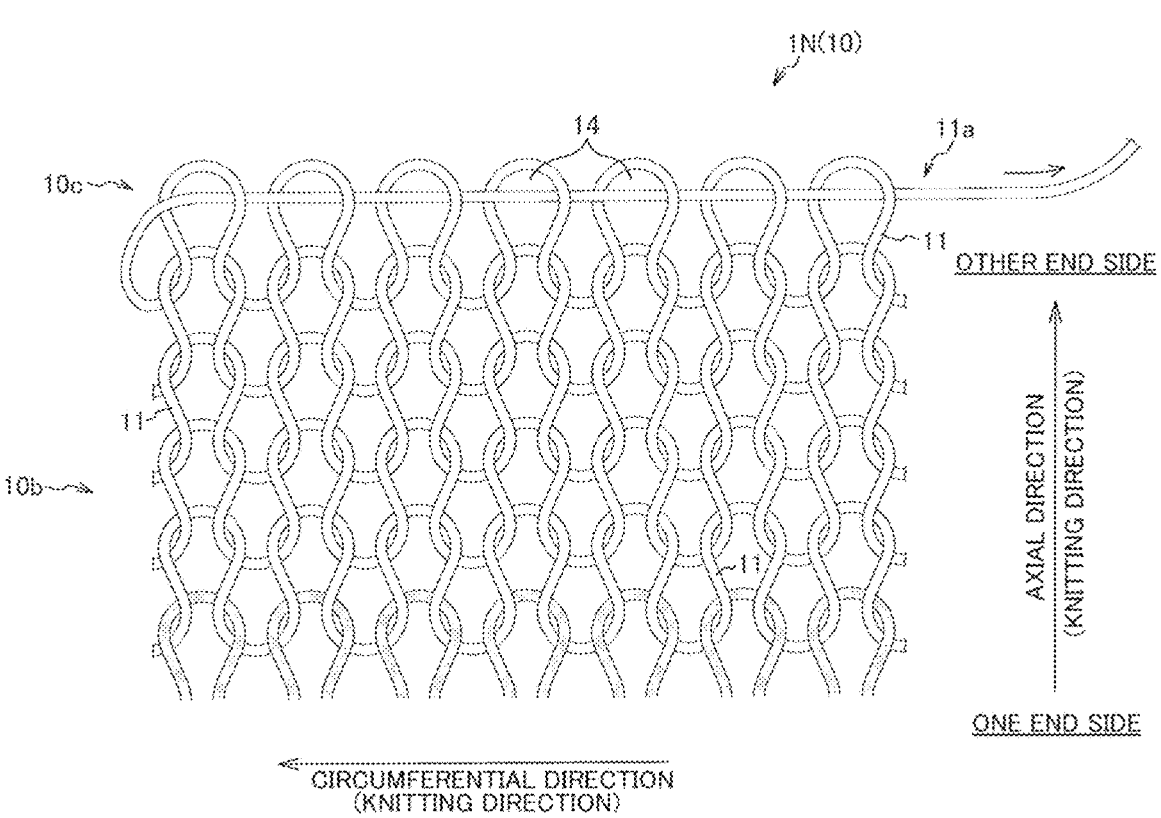
FIG. 16 is a schematic diagram for explaining a method for processing the end-part of the metal knit portion.

While FIG. 13 illustrate the examples in which the treatment is performed on the end part on the knitting end side, the same end-part treatment may be performed on the end part on the knitting start side. In addition, the loop 14 around which the end part 11*a* is wound may be a sinker loop. Furthermore, the end part 11*a* may be inserted into a plurality of loops and wound around the plurality of loops at once. Alternatively, after the end part 11*a* is sequentially inserted into a plurality of loops as illustrated in FIG. 16, the end part 11*a* may be wound around an appropriate loop as illustrated in FIG. 13. When the end part 11*a* is sequentially inserted into a plurality of loops 14, each loop at the subsequent stage does not drop from each loop at the previous stage and thus it is possible to effectively prevent fraying.

In this example, the length of the implant 1 in the circumferential direction (or the length in the width direction) at an axial end part of the implant 1 is maintained to be nearly equal to those of the implant 1 in the circumferential direction at other parts of the implant 1 in the axial direction. In addition, in this example, since the end-part treatment is performed using the metal string 11 forming the metal knit portion 10, it is not necessary to newly prepare a material for the end-part processing.

SIXTH EXAMPLE OF END-PART PROCESSING

Figure 14:
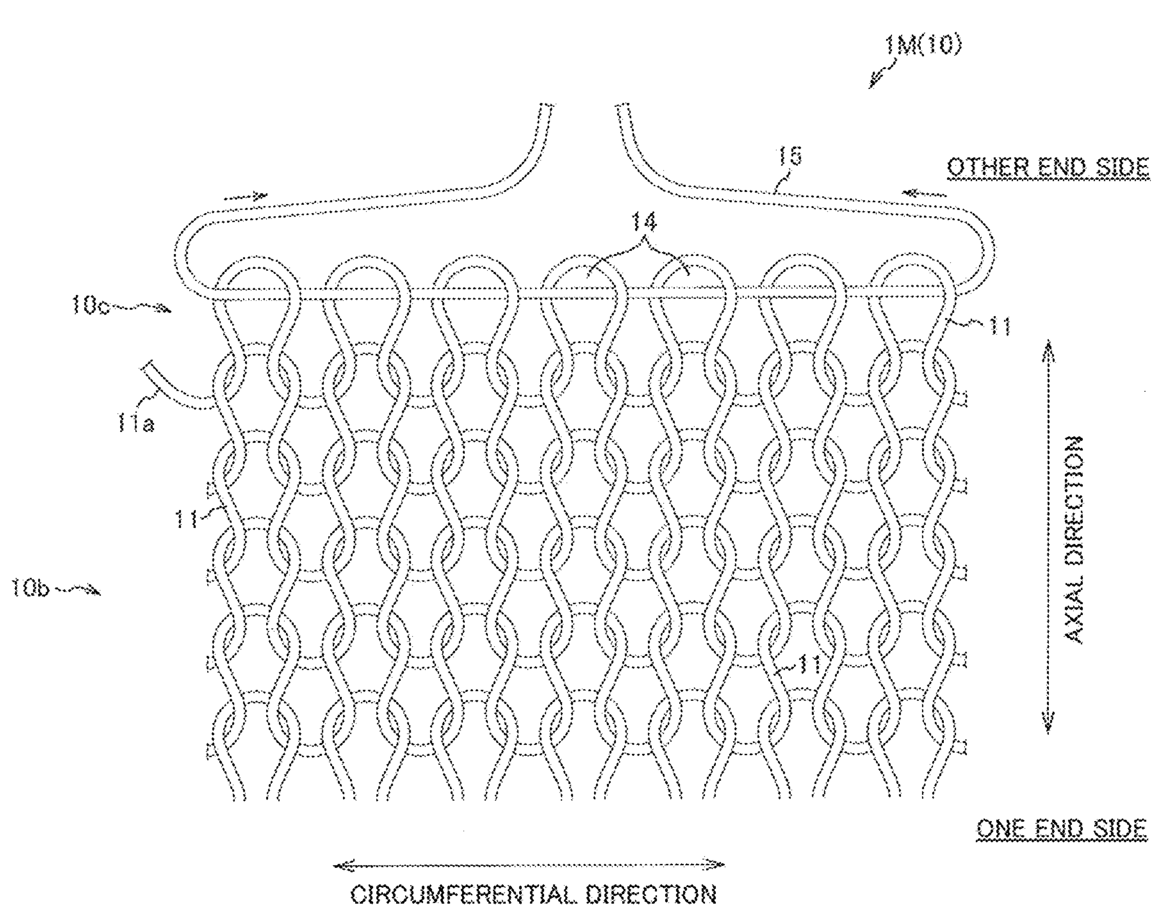
FIG. 14 is a schematic diagram illustrating an example of the end-part processing of the metal knit portion.
Figure 15:
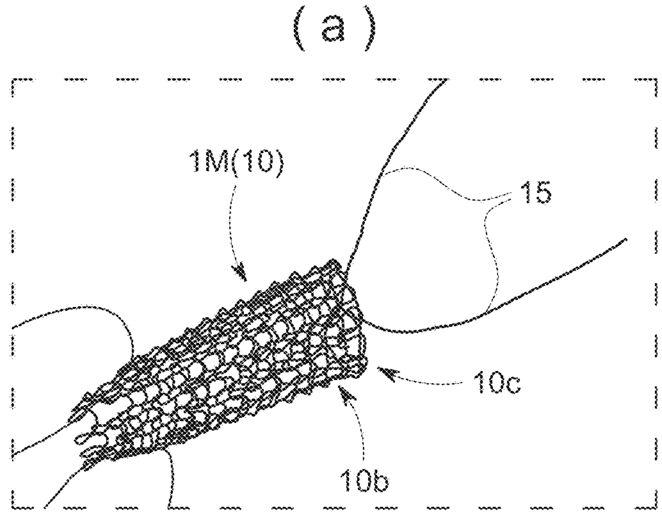
FIGS. 15(*a*) to 15(*c*) are diagrams illustrating a procedure for processing the end-part of the metal knit portion in real images.
Figure 15:
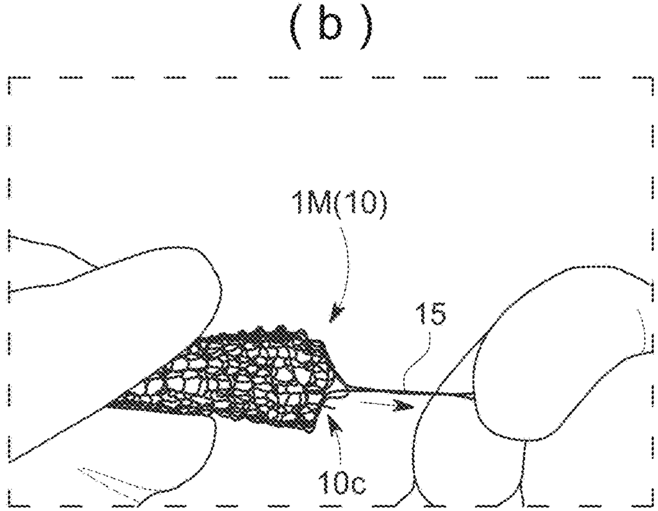
Figure 15:
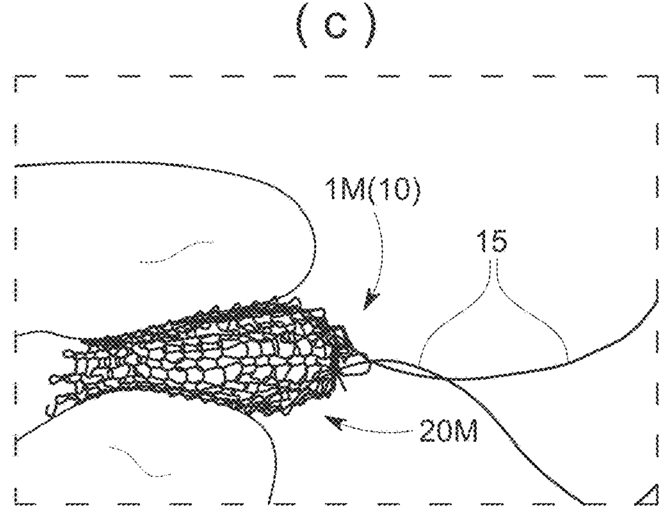

FIG. 14 is a schematic diagram illustrating an example of the end-part processing of the metal knit portion. FIGS. 15(*a*) to 15(*c*) are diagrams illustrating an end-part processing procedure for the metal knit portion in real images.

An implant 1M according to this example is processed as end-part processing 20M to sequentially insert a string (wire 15) different from the metal string 11 into a plurality of loops (the needle loops 14, sinker loops) positioned at an axial end part of the metal knit portion 10 and pull and tighten the string to reduce the diameter of the axial end part of the metal knit portion 10. FIG. 14 illustrates the end part 10*b* of the metal knit portion on the knitting end side as an example.

It is preferable that the wire 15 be a metal string made of the same material as the metal string 11 constituting the metal knit portion 10. However, the wire 15 may be made of another metal material having biocompatibility or may be a non-metal string having biocompatibility.

As illustrated in FIG. 14, it is desirable that loops into which the wire 15 is inserted be all needle loops 14 positioned at the axial edge 10*c* of the metal knit portion 10, that is, all needle loops 14 forming the last stage of the metal knit portion 10. However, it suffices to insert the wire 15 into a plurality of loops in quantity and position that can reduce the diameter of the end part 10*b* of the metal knit portion 10 to such an extent that it is possible to prevent fraying. It suffices to reduce the diameter of the end part 10*b* of the metal knit portion 10 to such an extent that it is possible to prevent fraying.

For example, as illustrated in FIGS. 14 and 15(*a*), after the wire 15 is sequentially inserted into all the needle loops 14, the wire 15 is pulled toward a direction indicated by arrows in FIGS. 14 and 15(*b*) to minimize the diameter of the axial end part 10*b* of the metal knit portion 10 as illustrated in FIG. 15(*c*).

According to this example, since the wire 15 is inserted into the plurality of needle loops 14, even when the end part 11*a* of the metal string 11 is pulled toward the distal end, each needle loop 14 in which the wire 15 has been inserted does not drop from each loop at the previous stage. Therefore, stitches of the metal knit portion 10 are not unraveled. In addition, since the wire 15 is used to reduce the diameter of the axial end part 10*b* of the metal knit portion 10, parts of the metal string 11 at the corresponding part are plastically deformed and entangled (or meshed) with each other and thus it is possible to effectively prevent the end part 10*b* from fraying.

When the wire 15 is pulled to reduce the diameter of the end part 10*b*, the end-part treatment may not be particularly performed on the end part 11*a* of the metal string 11 in a state in which the end part 11*a* remains cut. Alternatively, similarly to FIG. 13, the end part 11*a* of the metal string 11 may be wound around an appropriate loop.

The end-part treatment illustrated in FIGS. 14 and 15 may be performed on the end part on the knitting start side. In this case, it suffices to sequentially insert the end part of the metal string 11 on the knitting start side into loops (needle loops or sinker loops) positioned at the one end part (the end part on the knitting start side) of the metal knit portion 10 in the axial direction and pull and tighten the end part of the metal string 11.

SEVENTH EXAMPLE OF END-PART PROCESSING

A seventh example of the end-part processing is described based on FIG. 16 with reference to FIGS. 14 and 15.

FIG. 16 is a schematic diagram for explaining a method for processing an end-part of a metal knit portion. FIG. 16 is a diagram corresponding to FIGS. 14 and 15(*a*).

An implant 1N according to this example is processed as the end-part processing to sequentially insert the end part (the end part 11*a*) of the metal string 11 into a plurality of loops (the needle loops 14, sinker loops) positioned at an axial end part of the metal knit portion 10 and pull and tighten the end part toward a direction indicated by an arrow in FIG. 16 to reduce the diameter of the axial end part of the metal knit portion 10 as illustrated in FIG. 15(*c*).

In this example, the end-part processing corresponding to FIGS. 14 and 15 is performed using the metal string 11 forming the metal knit portion 10 instead of the wire 15. Basic configurations in this example are as described above, therefore detailed explanations thereof are omitted.

In this example, since the end-part treatment is performed using the metal string 11 forming the metal knit portion 10, it is not necessary to newly prepare a material for the end-part processing.

SURGERY APPLICATION EXAMPLE

Figure 9:
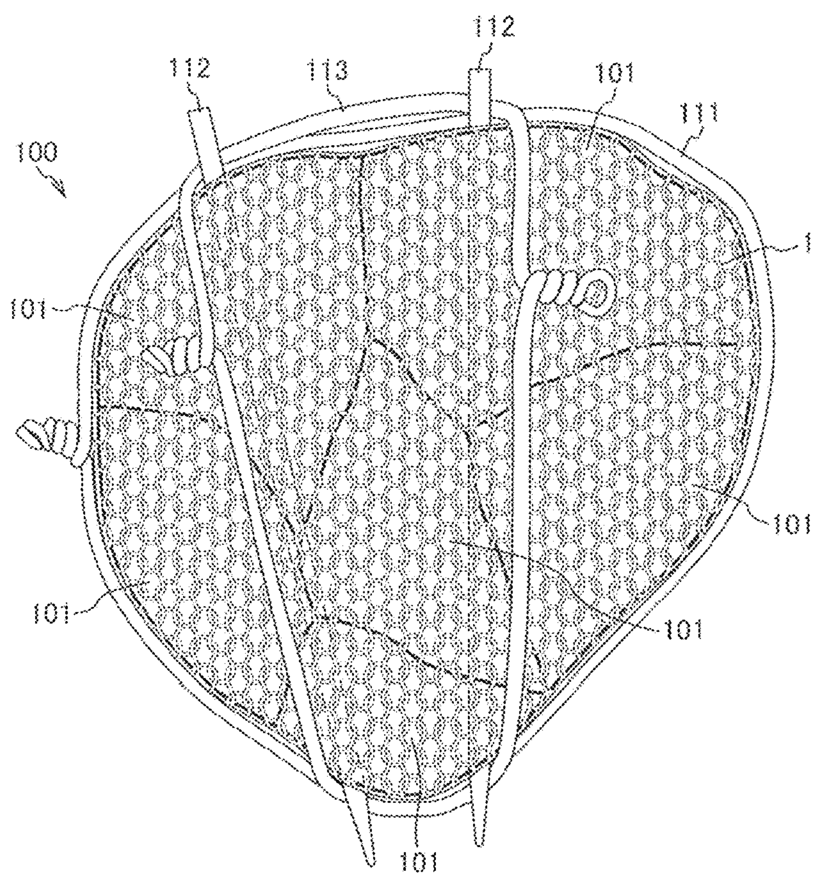
FIG. 9 is a schematic diagram illustrating a case where the implant according to the present embodiment is applied to treatment for a patella crush fracture.

FIG. 9 is a schematic diagram illustrating a case where the implant according to the present embodiment is applied to treatment for a patella crush fracture.

A treatment example illustrated in FIG. 9 is an example in which the implant illustrated in FIG. 1 is used as a support to treat a crushed and fractured patella according to tension band wiring (TBVV) in which an existing implant (a Kirschner wire and a mild steel wire) is used.

The implant 1 covers the entire anterior surface of a patella 100. A mild steel wire 111 is provided on the implant 1 and extends around the patella 100. The mild steel wire 111 collects many crushed bone fragments 101, 101, . . . together as a whole. The mild steel wire 111 fixes the implant 1 in a mesh form according to the present embodiment to the patella 100. Kirschner wires 112, 112 inserted through the bone fragments 101, 101, . . . in a vertical direction in FIG. 9 reduce and fix the bone fragments 101, 101, . . . . The Kirschner wires 112, 112 are inserted into the bone fragments 101, 101, . . . through the implant 1. A mild steel wire 113 as a tension band applies compressive force for collecting the bone fragments 101, 101, . . . of the patella 100 together and fastening the patella 100.

The implant 1 in a mesh form keeps the bone fragments 101, 101, . . . in a gathered state. The implant 1 allows fixation of small bone fragments, which is difficult with the TBW method. The implant 1 covers the entire anterior surface of the patella 100 to prevent the small bone fragments from rising toward the anterior surface side and keep each of the small bone fragments in close contact with the other bone fragments.

When a fractured part has a bone defect, the implant 1 presses and fixes artificial bone powder filled in the defect part together with bone fragments. The implant 1 prevents outflow of the artificial bone powder filled in the defect part.

Since the implant 1 has many holes in the entire surface, steel wires, nails, and the like can be inserted into the implant 1 from any position on the implant 1. The implant 1 can be fixed to a fractured part by a steel wire inserted in the implant 1 and/or a nail inserted in the implant 1.

The implant 1 according to the present embodiment is particularly suitable for treatment of not only the patella fracture illustrated in FIG. 9 but also fractures of an olecranon, a calcaneus, a greater trochanter of femur, and the like.

The implant 1 is left in a living body until at least treatment of the fractured part is completed. The implant 1 may be left in a living body even after the fractured part is completely healed.

Although the implant 1 may be used alone for bone fracture treatment, the implant 1 may be used in combination with another existing implant plate and/or a steel wire or the like. In this case, the implant 1 collaborates with other implants such as a Kirschner wire and a plate to ensure the strength required to fix a fractured part.

In the surgery application example described above, the example in which the implant is used while covering the anterior surface of a patella is described. However, the implant 1 may be used in a mode in which the implant 1 is wrapped around an entire fractured part and surrounds the entire fractured part.

The implant 1 according to the present embodiment can be fixed to another existing implant or a fractured part by being combined with one or any of the steel wires described above, binding bands, bolts, medical staplers, adhesives, and the like.

<Effect>

Since the metal knit portion 10 of the implant 1 is formed by knitting a metal string, the metal knit portion 10 can be flexibly curved or bent and deformed for use. Therefore, the metal knit portion 10 can be used in a desired shape according to the shape and the state of a fractured part.

Since the entire metal knit portion 10 of the implant 1 is in a mesh form, a steel wire, a bolt, and the like can be inserted into the metal knit portion 10 from any position on the metal knit portion 10. Therefore, even when the implant 1 is used together with an existing steel wire or a plate, both of the implant 1 and the steel wire or the plate can be used in combination without concern on the interference between the steel wire itself or a bolt for fixing the plate and the implant 1.

Conventional implants such as plates, nails, and the like are highly rigid and thus may receive stress intensively and repeatedly. In such a case, the conventional implants such as plates, nails, and the like may be damaged in a human body. However, since the metal knit portion 10 is made of a knitted fabric, it is unlikely that only a specific part of the metal knit portion 10 receives stress intensively. Therefore, it solves the problem that the implant is damaged in a human body.

The metal knit portion 10 of the implant 1 is in a mesh form and thus can press and fix very small bone fragments.

The metal knit portion 10 of the implant 1 is formed of the metal string 11 and thus has strength required to be used the implant in a living body.

Meanwhile, the metal knit portion 10 is formed in a mesh form by knitting the fibrous metal string 11 and thus is more flexible than conventional implants such as metal plates.

Conventionally, a fixing material such as a plate, a pin, or the like that is used for bone fracture surgery has an elastic modulus (Young's modulus) largely different from those of living bodies. The fixing material described above is usually much more rigid than living bodies. Therefore, stress is intensively transmitted to the fixing material, and stress shielding occurs in which a load required for a living body is not transmitted. The stress shielding may cause bone atrophy or the like and cause a secondary bone fracture.

The implant 1 according to the present embodiment has a significantly reduced difference in strength (difference in Young's modulus) from bones in a living body as compared with the conventional implants. That is, even when the implant 1 according to the present embodiment is used at a site where a load is transmitted to a bone, the implant 1 can transmit stress required for the living body to the bone of the living body and thus can prevent or reduce occurrence of stress shielding.

Second Embodiment

Figure 10:
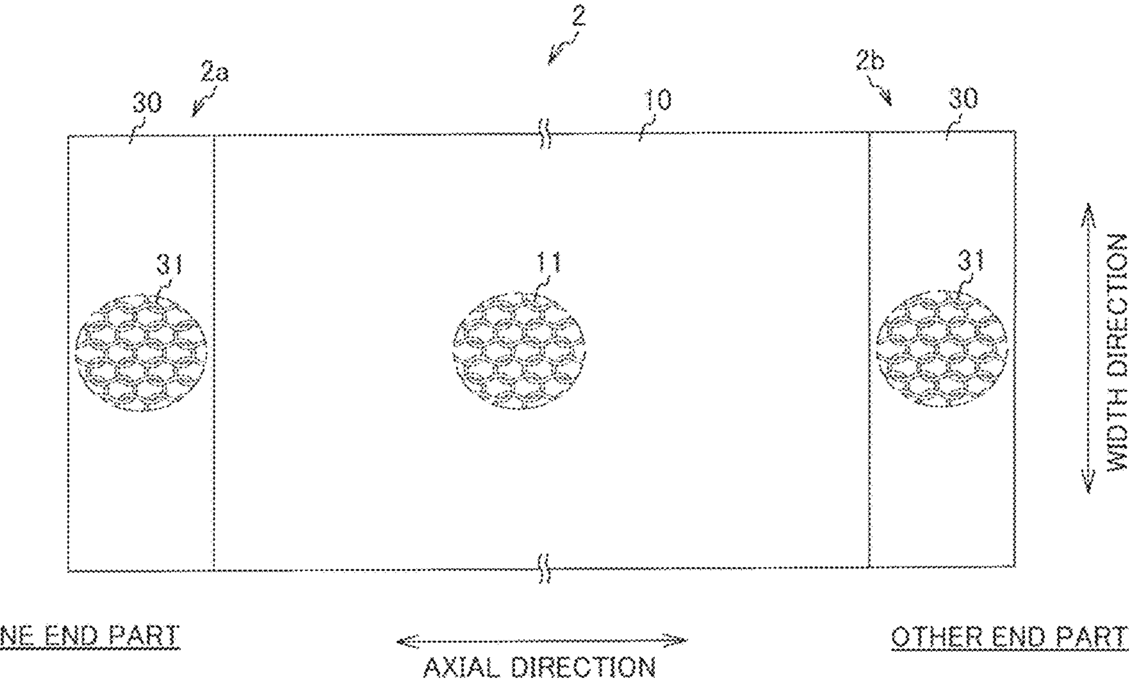
FIG. 10 is a diagram illustrating a schematic configuration of an implant according to a second embodiment of the present invention.

FIG. 10 is a diagram illustrating a schematic configuration of an implant according to a second embodiment of the present invention.

An implant 2 according to the present embodiment includes the metal knit portion 10 described in the first embodiment and a resin knit portion 30 (a resin knit mesh portion) formed by knitting a resin string 31 constituted by one or a plurality of biocompatible resin string elements. In the following descriptions, explanations of configurations identical to those in the first embodiment are omitted as appropriate.

In the implant 2, the metal knit portion 10 and the resin knit portion 30 are knitted to be continuous in the axial direction. The metal knit portion 10 and the resin knit portion 30 are knitted into a cylindrical shape by circular knitting.

In this case, the metal knit portion 10 and the resin knit portion 30 are knitted from one end side to the other end side in the axial direction.

The implant 2 illustrated in FIG. 10 has three knit portions (two resin knit portions 30 and 30 and one metal knit portion 10). The resin knit portions 30 are provided at one end part 2*a* and the other end part 2*b* of the implant 2 in the axial direction, and the metal knit portion 10 is provided at an intermediate part (between the resin knit portions 30 and 30) of the implant 2 in the axial direction.

The number of metal knit portions 10 included in the implant 2 may be 2 or more. The number of resin knit portions 30 included in the implant 2 may be 3 or more. It is desirable that the resin knit portions 30 be provided at the one end part 2*a* and the other end part 2*b* of the implant 2 in the axial direction.

<Configuration of Resin Knit Portion>

As the resin knit portions 30, biocompatible resin that can be left in a human body is used. As the resin string 31, a surgical suture can be used. Specifically, a suture made of polypropylene, polyester, nylon, or the like as a non-absorbable material can be used as the resin string 31. A suture made of polyglycolic acid, polylactic acid, polydioxanone, caprolactone, or the like as an absorbable material can be used as the resin string 31.

It is desirable that the resin string 31 be made of thermoplastic resin. By using thermoplastic resin for the resin string 31, parts of the resin string 31 can be melted by heating and can adhere to each other. Since a portion where the parts of the resin string 31 are melted and bonded to each other does not fray, it is possible to prevent the entire implant 2 from fraying. In addition, cutting the portion where the parts of the resin string 31 are melted and bonded to each other can prevent the generation of lint (U-shaped cut pieces) of the resin string 31. Therefore, it is possible to easily obtain the implant 2 having an axial length optimal for bone fracture treatment without generating lint. Each of the resin knit portions 30 functions as means for forming, in the implant 2, an end-part processing portion processed to prevent the implant 2 from fraying. At the time of cutting the implant 2, it suffices to melt the resin string 31 around cut parts of the resin knit portions 30 and it is not necessary to melt the entire resin knit portions 30.

As the resin string 31, biodegradable resin may be used. By using biodegradable resin for the resin string 31, only the metal knit portion 10 is left in a living body after the resin string is biodegraded.

The resin string 31 constituting the resin knit portions 30 may be constituted by a single resin string element (corresponding to the metal string element 12 illustrated in FIG. 2) in the same manner as the metal string 11 (see FIG. 2(*a*)), or may be constituted by a plurality of resin string elements that are non-stranded wire strings (see FIG. 2(*b*)), or may be constituted by a stranded wire string made by twisting a plurality of resin string elements together (see FIG. 2(*c*)).

As each of the resin string elements, for example, a round wire string with a circular sectional shape is used. When the resin string element is a round wire string, it is preferable that the wire diameter (diameter) of the resin string element be, for example, in a range from Ø0.06 mm to Ø0.70 mm. When the resin string 31 is constituted by a plurality of resin string elements, it is preferable that the outer diameter (diameter) of the resin string 31 be equal to or smaller than Ø0.70 mm.

The sectional shape of the resin string element may be other than a circular sectional shape. The wire diameter of the resin string element may be equal to or different from the wire diameter of the metal string element 12. The sectional shape of the resin string element may be the same as or different from the sectional shape of the metal string element 12. The number of metal string elements 12 constituting the metal string 11 may be the same as or different from the number of resin string elements constituting the resin string 31.

The type of a knitted fabric of the resin knit portions 30, the width and the height of each stitch of the resin knit portions 30, the density (looseness/roughness) of the stitches of the resin knit portions 30, and the like are set to be equal to those of the metal knit portion 10, but may be different from those of the metal knit portion 10.

The resin knit portions 30 and 30 positioned at each end part of the implant 2 in the axial direction can be subjected to the end-part treatment as illustrated in FIGS. 5 to 8 for the purpose of preventing the resin knit portions 30 from fraying.

When thermoplastic resin is used for the resin string 31, fraying of the metal knit portion 10 and the resin knit portions 30 is prevented by melting parts of the resin string 31 to bond the parts of the resin string 31 to each other and cutting the melted and bonded parts. In this case, it is not necessary to perform the end-part treatment illustrated in FIGS. 5 to 8 for the purpose of preventing the metal knit portion 10 from fraying.

The resin knit portions 30 and 30 positioned at the end parts of the implant 2 may be subjected to the end-part treatment as illustrated in FIGS. 7 and 8 for the purpose of adding a function. In a case where an end part of the implant 2 in the axial direction is tapered as illustrated in FIG. 7, an end part of the resin knit portion 30 may be deformed into a tapered shape and hardened after being softened by heating. The hook-and-loop fasteners 20H or the snap coupling members 20J illustrated in FIG. 8 can be attached to the resin knit portion 30 by using an adhesive, or using the melted resin knit portion 30 as an adhesive, or melting both the hook-and-loop fasteners 20H or the snap coupling members 20J and the resin knit portion 30 to bond the hook-and-loop fasteners 20H or the snap coupling members 20J to the resin knit portion 30.

<Manufacturing of Implant>

A part of a manufacturing process of the implant 2 will be described with reference to FIGS. 4 and 11.

Figure 11:
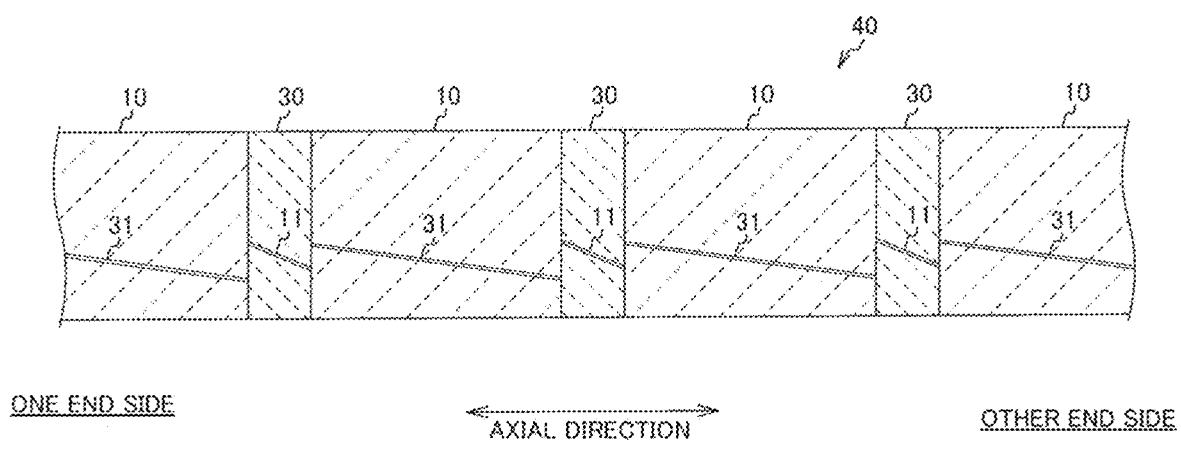
FIG. 11 is a schematic diagram illustrating a schematic configuration of a knit member according to the second embodiment that is produced at Step S1 in FIG. 4.

FIG. 11 is a schematic diagram illustrating a schematic configuration of a knit member according to the second embodiment that is produced at Step S1 in FIG. 4.

In a knit member producing process at Step S1, a knit member 40 is produced. The knit member 40 includes a plurality of resin knit portions 30 and a plurality of metal knit portions 10 and has a structure in which the resin knit portions 30 and the metal knit portions 10 are knitted to be continuous and alternately arranged in the axial direction. The implant 2 is produced by cutting the knit member 40 that is the precursor of the implant 2.

As a circular knitting machine for manufacturing the knit member 40 described above, the "wire mesh knitting machine" described in Utility Model Registration No. 3178575 can be used. At Step S1, a process of circularly knitting the metal string 11 to produce the metal knit portion 10 and a process of circularly knitting the resin string 31 to produce the resin knit portion 30 are alternately performed to produce the knit member 40.

The metal string 11 passes in the axial direction of the resin knit portions 30 each of which is formed intermittently in the axial direction. The metal string passing within each resin knit portion 30 is a metal string constituting the metal knit portions 10 and 10 knitted at both axial end parts of the resin knit portion 30. That is, the metal string 11 constituting the two adjacent metal knit portions 10 is continuous in the resin knit portion 30 positioned between both of the metal knit portions 10 and 10. The resin knit portion 30 is produced without cutting the metal string 11 constituting the immediately preceding metal knit portion 10.

The resin string 31 passes in the axial direction of the metal knit portions 10 each of which is formed intermittently in the axial direction. The resin string passing within each metal knit portion 10 is a resin string constituting the resin knit portions 30 and 30 knitted at both axial end parts of the metal knit portion 10. That is, the resin string 31 constituting the two adjacent resin knit portions 30 is continuous in the metal knit portion 10 positioned between both of the resin knit portions 30 and 30. The metal knit portion 10 is produced without cutting the resin string 31 constituting the immediately preceding resin knit portion 30.

The metal string 11 and the resin string 31 pass in the axial direction on the inner circumferential side of the resin knit portion 30 and the metal knit portion 10, respectively.

At Step S1, the knit member 40 that is longer than the implant 2 in the axial direction is obtained. Further, at Step S1, the knit member 40 in which the number of metal knit portions 10 and the number of resin knit portions 30 are larger than those of the implant 2 is obtained. Since the knit member 40 has a structure in which the metal string 11 passes in the resin knit portions 30 and a structure in which the resin string 31 passes in the metal knit portions 10, the circular knitting machine can be operated continuously regardless of the length of the implant 2 as the final product in the axial direction and thus the efficiency of manufacturing the implant 2 is improved.

In a cutting process at Step S3, the knit member 40 is removed from the circular knitting machine. That is, the knit member 40 with a predetermined length in the axial direction is obtained by cutting the metal string 11 and the resin string 31.

Step S5 and Step S7 are performed as needed.

In an end-part treatment process at Step S9, the implant 2 with a required length in the axial direction is obtained by cutting an appropriate axial part of the resin knit portion 30 of the knit member 40 in the width direction. Since the metal string 11 passes in the resin knit portions 30, even when the resin knit portion 30 is cut in the width direction, chips (U-shaped cut pieces) of the metal string 11 are not generated. Further, when the resin knit portion 30 is cut after the thermoplastic resin string 31 is melted by heating, the melted resin adheres to the metal string 11 to prevent the metal string 11 in the resin knit portions 30 from being separated from the resin knit portions 30. Since a portion where parts of the resin string 31 are melted and bonded to each other does not fray, the entire implant 2 is prevented from fraying.

Since the treatment described above is performed to produce the implant 2, the resin string 31 passes (exists) in the metal knit portions 10 of the implant 2 and the metal string 11 passes (exists) in the resin knit portions 30 in the same manner as the knit member 40.

In the end-part treatment process at Step S9, the end-part treatment illustrated in FIGS. 5 to 8 is performed as needed.

Figure 12:
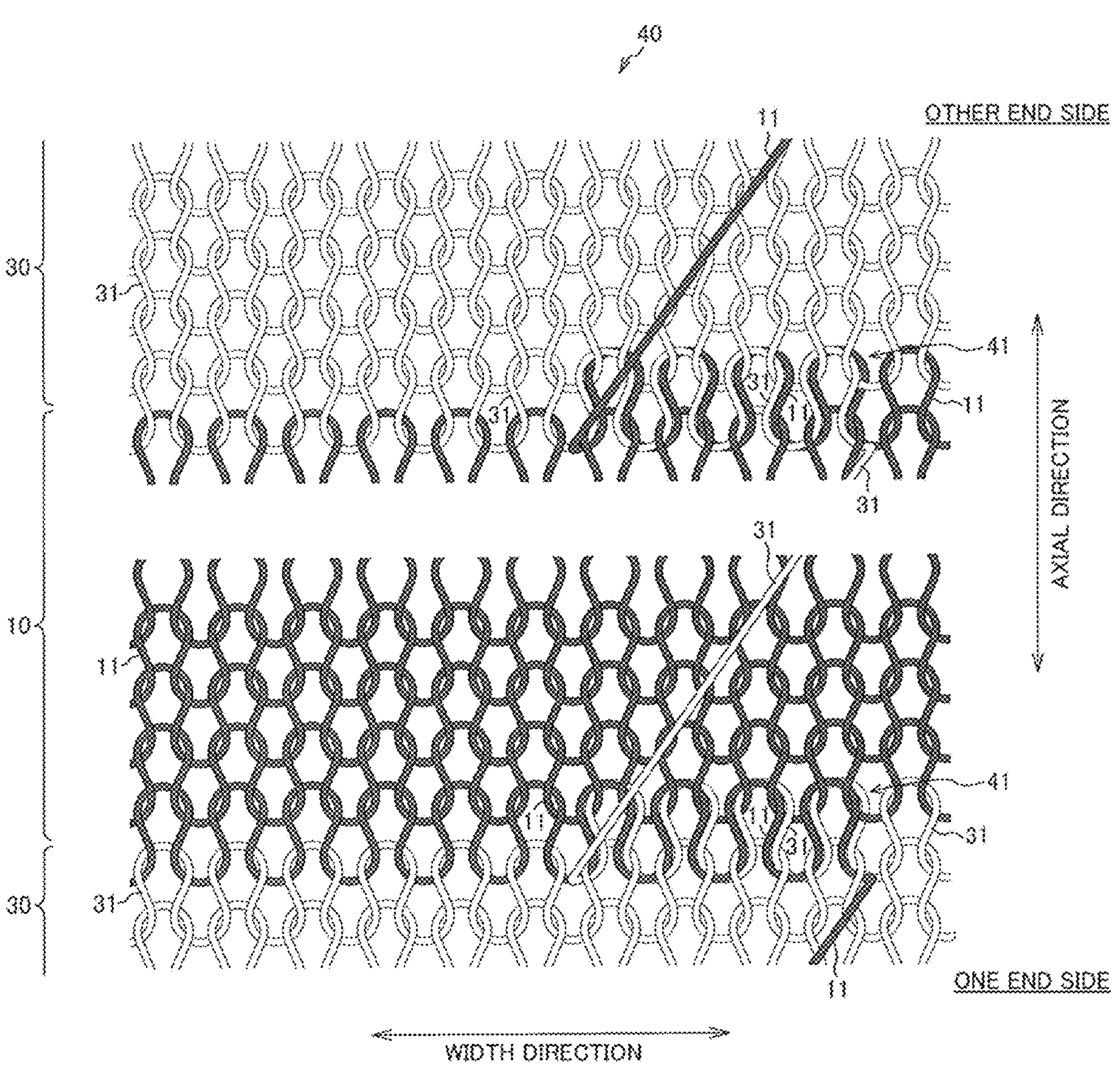
FIG. 12 is a partially enlarged view of the knit member.

FIG. 12 is a partially enlarged view of the knit member.

The knit member 40 includes an overlapping portion 41 where a knitting end part (an end part) of one knit portion (for example, the metal knit portion 10) overlaps a knitting start part (a start part) of the next knit portion (for example, the resin knit portion 30). The overlapping portion 41 is formed at a portion where the metal knit portion 10 and the resin knit portion 30 are shifted (switched) to each other. For the overlapping portion 41, the metal string 11 and the resin string 31 are simultaneously knitted. In the overlapping portion 41, a plurality of loops (needle loops and sinker loops) arranged in the width direction are formed by the metal string 11 and the resin string 31 such that it is possible to stabilize the shapes, sizes, and looseness (density), and the like of stitches as the entire knit member 40.

The overlapping portion 41 is formed by an appropriate number of loops such as three loops or more.

<Effect>

According to the present embodiment, effects identical to those in the first embodiment can be attained.

When the implant 2 includes two or more metal knit portions 10, it is possible to obtain an implant with a desirably adjusted length in the axial direction by melting an appropriate axial part of the resin knit portion 30 and cutting along the width direction at a cure site without generating cut pieces.

In a case where the resin knit portion 30 is knitted at Step S1, even when the metal string 11 forming the immediately preceding metal knit portion 10 is cut, it is possible to produce the knit member 40. Similarly, in a case where the metal knit portion 10 is knitted at Step S1, even when the resin string 31 forming the immediately preceding resin knit portion 30 is cut, it is possible to produce the knit member 40.

EXAMPLES OF ASPECTS OF PRESENT INVENTION AND SUMMARY OF ACTIONS AND EFFECTS

<First Aspect>

The present aspect provides an implant for bone fracture treatment that covers bone fragments gathered at a site to be treated for a bone fracture in a living body and reduces and fixes the site invasively. In each of the implants 1 and 2, the metal string 11 constituted by one or a plurality of biocompatible metal string elements 12 has the metal knit portion 10 knitted in a cylindrical shape by circular knitting.

Since the metal knit portion is formed by knitting the metal string, the metal knit portion can be flexibly curved or bent and deformed for use. Therefore, the metal knit portion can be used in a desirable shape according to the shape and the state of a fractured part.

The metal knit portion is a three-dimensional porous structure with a predetermined thickness and can cover bone fragments gathered at a site to be treated for a bone fracture. The metal knit portion can keep even very small bone fragments, which were conventionally difficult to be fixed, in close contact with other bone fragments.

The metal knit portion described in the present aspect is in a mesh form and thus a steel wire, a bolt, and the like can be inserted into the metal knit portion from any position on the metal knit portion. Therefore, even when the implant is used together with an existing steel wire or a plate, both the implant and the existing steel wire or the plate can be used in combination without concern on the interference between the steel wire itself or the bolt for fixing the plate and the implant.

Since the metal knit portion is formed by knitting the metal string, the metal knit portion has strength necessary to be used as an implant. Meanwhile, the metal knit portion has a significantly reduced difference in strength (difference in Young's modulus) from bones in a living body and thus it is possible to prevent or reduce occurrence of stress shielding.

According to the present aspect, it is possible to provide a new implant for bone fracture treatment that can simply and securely fix bone fragments.

<Second Aspect>

In the implant 2 according to the present aspect, the resin string 31 constituted by one or a plurality of biocompatible resin string elements has the resin knit portion 30 knitted in a cylindrical shape by circular knitting, and the metal knit portion 10 and the resin knit portion 30 are knitted to be continuous in the axial direction.

Thermoplastic resin can be used for the resin string. Biodegradable resin can be used for the resin string. It is possible to add various functions to the implant according to the type of resin constituting the resin string.

For example, when thermoplastic resin is used for the resin string, it is possible to prevent the metal string from fraying by melting the resin string.

<Third Aspect>

In the implant 2 according to the present aspect, the resin string 31 constituting two adjacent ones of the resin knit portions 30 and 30 is continuous in the metal knit portion 10 positioned between both of the resin knit portions.

According to the present aspect, since the metal knit portion and the resin knit portions are produced without cutting the resin string, the efficiency of manufacturing the implant is improved.

<Fourth Aspect>

In the implant 2 according to the present aspect, the metal string 11 constituting two adjacent ones of the metal knit portions 10 and 10 is continuous in the resin knit portion 30 positioned between both of the metal knit portions.

According to the present aspect, since the resin knit portion and the metal knit portions are produced without cutting the metal string, the efficiency of manufacturing the implant is improved. In addition, even when an appropriate part of the resin knit portion in the axial direction is cut along the width direction, cut pieces of the metal string are not generated.

<Fifth Aspect>

In each of the implants 1 and 2 according to the present aspect, end-part processing (20, 30) that prevents the metal knit portion from fraying is performed on an end part in the axial direction.

The end-part processing includes, for example, folding the end part of the implant in three, attaching various fastening tools to the end part of the implant, hardening the end part of the implant with resin, and the like. In addition, it is also possible to prevent the metal knit portion from fraying by knitting the resin knit portion 30 such that the resin knit portion 30 is continuous to an axial end part of the metal knit portion.

<Sixth Aspect>

In the implant 1 according to the present aspect, the end-part processing 20 (FIGS. 14 to 16) is processing of sequentially inserting an end part (the end part 11*a*) of the metal string 11 or another string (the wire 15) into a plurality of loops (the needle loops 14, sinker loops) positioned at the end part 10*b* of the metal knit portion 10 in the axial direction and pulling and tightening the end part of the metal string 11 or the string to reduce the diameter of the end part of the metal knit portion.

According to the present aspect, since the string is inserted in the loops, stitches of the metal knit portion do not fall out. In addition, by reducing the diameter of the axial end part of the metal knit portion, parts of the metal string at the corresponding part are plastically deformed and entangled (or meshed) with each other, and thus it is possible to effectively prevent the end part from fraying.

<Seventh Aspect>

The present aspect provides a manufacturing method of the implant 1 or 2 for bone fracture treatment that covers bone fragments gathered at a site to be treated for a bone fracture in a living body and reduces and fixes the site invasively.

The manufacturing method of an implant includes a process (Step S1) of producing the knit member 40 in which a metal knit portion and a resin knit portion are knitted to be continuous in an axial direction by alternately performing a process of producing the metal knit portion 10 by knitting the metal string 11 constituted by one or a plurality of biocompatible metal string elements 12 into a cylindrical shape by circular knitting, and a process of producing the metal knit portion 30 by knitting the resin string 31 constituted by one or a plurality of biocompatible resin string elements into a cylindrical shape by circular knitting. The manufacturing method further includes a process (Step S9) of cutting an appropriate part of the resin knit portion in the axial direction.

According to the present aspect, since the implant is obtained by cutting the resin knit portion after producing the knit member in which the metal knit portion and the resin knit portion are continuous in the axial direction, the efficiency of manufacturing the implant is improved.

REFERENCE SIGNS LIST

1 implant, 1*a* one end part, 1*b* other end part, 2 implant, 2*a* one end part, 2*b* other end part, 10 metal knit portion, 10*a* one end part, 10*b* other end part, 10*c* edge, 11 metal string, 11*a* end part, 12 metal string element, 13 inner circumferential face, 14 needle loop, 15 wire, 20A, 20E, 20F end-part processing portion, 20B to 20D, 20G fastening tool, 20H hook-and-loop fastener, 20J snap coupling member, 21 base, 30 resin knit portion, 31 resin string, 40 knit member, 41 overlapping portion, 100 patella, 101 bone fragment, 111 mild steel wire, 112 Kirschner wire, 113 mild steel wire

The invention claimed is:

1. An implant for bone fracture treatment that covers bone fragments gathered at a site to be treated for a bone fracture in a living body and reduces and fixes the site invasively, comprising a metal knit portion formed by knitting a metal string constituted by one or a plurality of biocompatible metal string elements into a cylindrical shape by circular knitting; and a resin knit portion formed by knitting a resin string constituted by one or a plurality of biocompatible resin string elements into a cylindrical shape by circular knitting, wherein the metal knit portion and the resin knit portion are knitted to be continuous in an axial direction.

2. The implant for bone fracture treatment according to claim 1, wherein the resin knit portion comprises resin knit portions, and the metal knit portion is positioned between the resin knit portions.

3. The implant for bone fracture treatment according to claim 1, wherein the metal knit portion comprises metal knit portions, and the resin knit portion is positioned between the metal knit portions.

4. The implant for bone fracture treatment according to claim 1 wherein end-part processing is performed on an end part in an axial direction to prevent the metal knit portion from fraying.

5. The implant for bone fracture treatment according to claim 4, wherein the end-part processing comprises reducing a diameter of the end part of the metal knit portion.

6. The implant for bone fracture treatment according to claim 1 produced by a manufacturing method of an implant for bone fracture treatment that covers bone fragments gathered at a site to be treated for a bone fracture in a living body and reduces and fixes the site invasively, comprising:

a process of producing a knit member in which a metal knit portion and a resin knit portion are knitted to be continuous in an axial direction by alternately performing a process of producing the metal knit portion by knitting a metal string constituted by one or a plurality of biocompatible metal string elements into a cylindrical shape by circular knitting and a process of producing the resin knit portion by knitting a resin string constituted by one or a plurality of biocompatible resin string elements into a cylindrical shape by circular knitting; and a process of cutting an appropriate part of the resin knit portion in the axial direction.

7. The implant for bone fracture treatment according to claim 2, wherein the metal knit portion comprises metal knit portions, and the resin knit portion is positioned between the metal knit portions.

8. The implant for bone fracture treatment according to claim 2, wherein end-part processing is performed on an end part in an axial direction to prevent the metal knit portion from fraying.

9. The implant for bone fracture treatment according to claim 3, wherein end-part processing is performed on an end part in an axial direction to prevent the metal knit portion from fraying.

10. The implant for bone fracture treatment according to claim 7, wherein end-part processing is performed on an end part in an axial direction to prevent the metal knit portion from fraying.

11. The implant for bone fracture treatment according to claim 8, wherein the end-part processing comprises reducing a diameter of the end part of the metal knit portion.

12. The implant for bone fracture treatment according to claim 9, wherein the end-part processing comprises reducing a diameter of the end part of the metal knit portion.

13. The implant for bone fracture treatment according to claim 10, wherein the end-part processing comprises reducing a diameter of the end part of the metal knit portion.

* * * * *